United States Patent
Szybalski et al.

(10) Patent No.: US 6,864,087 B2
(45) Date of Patent: Mar. 8, 2005

(54) METHOD FOR CONVERTING SINGLE-COPY BAC VECTORS TO CONDITIONAL HIGH-COPY PBAC/ORIHC VECTORS

(75) Inventors: Waclaw Szybalski, Madison, WI (US); Jadwiga Wild, Madison, WI (US); Zdenka Hradecna, Brno (CZ)

(73) Assignee: Wisconsin Alumni Research Foundation, Madison, WI (US)

( * ) Notice: Subject to any disclaimer, the term of this patent is extended or adjusted under 35 U.S.C. 154(b) by 102 days.

(21) Appl. No.: 10/209,792

(22) Filed: Jul. 31, 2002

(65) Prior Publication Data

US 2003/0049665 A1 Mar. 13, 2003

Related U.S. Application Data

(60) Provisional application No. 60/309,125, filed on Jul. 31, 2001.

(51) Int. Cl.[7] ........................... C12N 15/69; C12N 15/70
(52) U.S. Cl. ..................... 435/476; 435/478; 435/320.1
(58) Field of Search ................................. 435/476, 478, 435/320.1, 488, 471

(56) References Cited

U.S. PATENT DOCUMENTS 5,874,259 A * 2/1999 Szybalski .................. 435/91.1

FOREIGN PATENT DOCUMENTS

WO    WO 00/78977    * 12/2000

OTHER PUBLICATIONS

Kim et al., Genome Research 8:404–412 (1998).*

* cited by examiner

Primary Examiner—James Ketter
Assistant Examiner—Nancy T. Vogel
(74) Attorney, Agent, or Firm—Quarles & Brady LLP

(57) ABSTRACT

A single-copy BAC vector (containing or lacking an insert) is converted in a host cell into a conditional high-copy BAC vector by introducing a conditional origin of replication into the single-copy BAC vector. The conditional ori is introduced by site-specific recombination between the SC BAC vector and a vector that contains the conditional ori. The host cell comprises a recombinase that recognizes a site-specific recombination site on both the BAC vector and the conditional ori vector. In the presence of the recombinase, the conditional ori-containing vector recombines into the BAC vector to produce a high-copy BAC vector that can be conditionally amplified by activating the conditional origin of replication on command.

16 Claims, 2 Drawing Sheets

```
       |  10        |  20        |  30        |  40        |  50        |  60
   1 GCGGCCGCAA GGGGTTCGCG TCAGCGGGTG TTGGCGGGTG TCCGGCTCG CTTAACTATG  60
  61 CGGCATCAGA GCAGATTGTA CTGAGAGTGC ACCATATGCG GTGTGAAATA CCGCACAGAT 120
 121 GCGTAAGGAG AAAATACCGC ATCAGGCGCC ATTCGCCATT CACGCTGCGC AACTGTTGGG 180
 181 AAGGGCCATC GGTGCGGCC TCTTCGCTAT TACCCCAGCT GGCGAAGCG GGATGTGCTG 240
 241 CAAGCGATT AAGTTGGGTA ACGCCAGGGT TTTCCCAGTC ACCACGTTGT AAAACGACGG 300
 301 CCAGTGAATT GTAATACGAC TCACTATAGG GCGAATTCGA GCTCGGTACC CGGGGATCCT 360
 361 CTAGAGTCGA CCTGCAGGCA TGCAAGCTTG AGTATTCTAT AGTGTCACCT AAATAGCTTG 420
 421 GCGTAATCAT CGTCATAGCT GTTTCCTGTG TGAAATTGTT ATCCGCTCAC AATTCCACAC 480
 481 AACATACGAG CCGGAAGCAT AAAGTGTAAA GCCTGGGGTG CCTAATGAGT GAGCTAACTC 540
 541 ACATTAATTG CGTTGCGCTC ACTGCCCGCT TTCCAGTCGG GAAACCTGTC GTGCCAGCTG 600
 601 CATTAATGAA TCGGCCAACG CGAACCCCTT GCGCCCatga gccatattca acgggaaacg 660
 661 tcttgctcga ggccgcgatt aaattccaac atggatgctg atttatatgg gtataaatgg 720
 721 gctcgcgata atgtcgggca atcaggtgcg acaatctatc gattgtatgg gaagcccgat 780
 781 gcgccagagt tgtttctgaa acatggcaaa ggtagcgttg caaatgatgt tacagatgag 840
 841 atggtcagac taaactggct gacggaattt atgcctcttc cgaccatcaa gcattttatc 900
 901 cgtactcctg atgatgcatg gttactcacc actgcgatcc ccgggaaaac agcattccag 960
 961 gtattagaag aatatcctga ttcaggtgaa aatattgctg atgcgctggc agtgttcctg 1020
1021 cgccggttgc attcgattcc tgtttgtaat tgtccttta acagcgatcg cgtatttcgt 1080
1081 ctcgctcagg cgcaatcacg aatgaataac ggtttggttg atgcgagtga ttttgatgac 1140
1141 gagcgtaatg gctggcctgt tgaacaagtc tggaaagaaa tgcataagct tttgccattc 1200
1201 tcaccggatt cagtcgtcac tcatggtgat ttctcacttg ataacctttat ttttgacgag 1260
1261 gggaaattaa taggttgtat tgatgttgga cgagtcggaa tcgcagaccg ataccaggat 1320
1321 cttgccatco tatggaactg cctcggtgag tttctctctt cattacagaa acgcttttt 1380
1381 caaaatatg gtattgataa tcctgatatg aataaattgc agtttcattt gatgctcgat 1440
1441 gagttttct aaGTGCCGAT CAAGGTCTCA TTTTCGCCAA AAGTTGGCCC ACGGGCTTCCC 1500
1501 GGTATCAACA CGGACACCAG GATTTATTTA TTCTGCCAAG TCATCTTCCG TCACAGGTAT 1560
1561 TTATTCGCGA TAAGCTCATG GAGCGGCGTA ACCGTCGCAC AGGAAGGACA GAGAAAGCGC 1620
1621 GGATCTGGGA AGTGACGGAC AGAACGGTCA GGACCTGGAT TGGGGAGGCG GTTGCCGCCG 1680
1681 CTGCTGCTGA CCGTGTCACG TTCTCTGTTC CGGTCACACC ACATACGTTC CGCCATTCCT 1740
1741 ATCGGATGCA CATGCTGTAT GCCGGTATAC CGCTGAAAGT TCTGCAAACC CTGATGGGCA 1800
1801 ATAAGTCCAT CAGTTCAACG CAAGTCTACA CGAAGCGTTT TGCCCTGAT GTGGCTGCCC 1860
1861 CGCACCGGGT GCAGTTTGCG ATGCCCGAGT CTGATGCCGT TGCCATGCTG AAACAATTAT 1920
1921 CCTGAGAATA AATGCCTTGG CCTTTATATG GAAATGTGGA ACTGAGTGGA TATGCTGTTT 1980
1981 TTGTCTGTTA AACAGAGAAG CTGGCTGTTA TCCACTGACA AGCCAACGAA ACAGTCGGGA 2040
2041 AAAATCTCCA TTATCGTAGA GATCCGCATT ATTAATCTCA GCGACCTGTG TAGCGTTTAT 2100
2101 AGGAAGTAGT GTTCTGTCAT CATGCCTTCA AGCGGTAACG AAAACGATTT GAATATGCCT 2160
2161 TCAGCAACAA TACAAATCTT CGTGCGGTGT TACGTTGAAG TGGAGCGCGAT TATCTCACCA 2220
2221 ATCGACAGAA CAACCTAATG AACACACAAC CATGATGTCG TCTGTCCTTT TACAGCCAGT 2280
2281 AGTGCTCGCC GCAGTCCACC GACAGGGCGA AGCCCTCCAg gccgccggcg ttgtggatac 2340
2341 cacgcggaaa acttggccct cactgacaga tgaggggcgg acgttgacac ttgaggggcc 2400
2401 gaccacccg gcgcggcgtt gacagatgag gggcaggctc gatttcggcc ggcgacgtgg 2460
2461 agctggccag cctcgcaaat cggcgaaaac gcctgatttt acgcgagtt cccacagatg 2520
2521 atgtggacaa gcctggggat aagtgccctg cggtattgac acttgaggg cgcgactgcc 2580
2581 gacagatgag gggcgcgatc cttgacactt gagggcaga gtgatgacag atgaggggcg 2640
2641 cacctattga catttgaggg gctgtccaca ggcagaaat ccagcatttg caaggggttc 2700
2701 cgcccgtttt tcggccaccg ctaacctgtc tttttaacctg ctttaaaacc aatatttata 2760
2761 aaccttgttt ttaaccaggg ctgagccctg gcgcgtgacc gcgcacgccg aaggggggtg 2820
2821 cccccccttc tcgaaccctc ccgggtatcG CGAGGAAGCA CCAGGCAACA GCACTTATAT 2880
2881 ATTCTCCTTA CACACGATCC CTGAAAAAAC TTCCCTTGGG GTTATCCACT TATCCACGGG 2940
2941 GATATTTTTA TAATTATTTT TTTTATAGTT TTTAGATCTT CTTTTTTAGA GCGCCTTGTA 3000
3001 GGCATGTCGT CGTAAACCTGT AGAAACGAGT AACCTCGGTG TGCCGTTGTA TGCCTGCTGT 3060
3061 GGATTGCTGC TGTGTCCTGC TTATCCACAA CATTTTCCGC ACCGTTATGT GGACAAAATA 3120
3121 CCTGGTTACC CAGGCCGTGC CGGCACGTTC CGCAATGCTT GCATAATGTG GCCTGTCAAA 3180
3181 TGCACGAAGC AGGGATTCTG CAAACCCTAT GCTACTCCGT CAAGCCGTCA ATTGTCTGAT 3240
3241 TCGTTACCAA TTATGACAAC TTGACGGCTA CATCATTCAC TTTTTCTTCA CAACCGGCAC 3300
3301 GAAACTCGCT CGGGCTGGCC CCGGTGCATT TTTTAAATAC TCGCGAGAAA TAGAGTTGAT 3360
3361 CGTCAAAACC AACATTGCGA CCGACGGTGG CGATAGGCAT CCGGGTAGTC CTCAAAAGCA 3420
3421 GCTTCGCCTG GCTGATACGT TGGTCCTCGC GCCAGCTTAA GACGCTAATC CCTAACTGCT 3480
3481 GGCGGAAAAG ATGTGACAGA CGCGACGGCG ACAACCAAAG ATCGTGTGCG ACCGTGGCCA 3540
3541 TATCAAGCTT ATCGAACCGG GCTGCATCCG ATGCAAGTGT GTCGCTGTCG ACGACCTGCC 3600
3601 GAACTCGGAC ATGAGGTTGC CCCGTATTCA GTGTCGCTGA TTTGTATTGT CTGAAGTTGT 3660
3661 TTTTACGTTA AGTTGATGCA GATCAATTAA TACGATACCT GCGTCATAAT TGATTATTTG 3720
3721 ACGTGGTTTG ATGGCCTCCA CGCACGTTGT GATATGTAGA TGATAATCAT TATCACTTTA 3780
3781 CGGGTCCTTT CCGGTGATCC GACACGTTAC GGGGCGGCGA CCTCGCGGGT TTTCGCTATT 3840
3841 TATGAAAATT TTCCGGTTTA AGGCGTTTCC GTTCTTCTTC GTCATAACTT AATGTTTTTA 3900
3901 TTTAAAATAC CCTCTGAAAA GAAAGGAAAC GACAAGTGCT GAAAGCGACC TTTTGGCCT 3960
3961 CTGTCGTTTC CTTTCTCTGT TTTTGTCCGT GGAATGAACA ATGGAAGTCC GAGCTCATCG 4020
4021 CTAATAACTT CGTATAgcat acattATACG AAGTTATATT CGAT         4064
```

FIG 2

SEQUENCE LISTING

```
<160> NUMBER OF SEQ ID NOS: 1

<210> SEQ ID NO 1
<211> LENGTH: 4064
<212> TYPE: DNA
<213> ORGANISM: Artificial Sequence
<220> FEATURE:
<223> OTHER INFORMATION: Description of Artificial Sequence: Plasmid
      pJW470

<400> SEQUENCE: 1
gcggccgcaa ggggttcgcg tcagcgggtg ttggcgggtg tcggggctgg cttaactatg      60
cggcatcaga gcagattgta ctgagagtgc accatatgcg gtgtgaaata ccgcacagat     120
gcgtaaggag aaaataccgc atcaggcgcc attcgccatt caggctgcgc aactgttggg     180
aagggcgatc ggtgcgggcc tcttcgctat tacgccagct ggcgaaaggg ggatgtgctg     240
caaggcgatt aagttgggta acgccagggt tttcccagtc acgacgttgt aaaacgacgg     300
ccagtgaatt gtaatacgac tcactatagg gcgaattcga gctcggtacc cggggatcct     360
ctagagtcga cctgcaggca tgcaagcttg agtattctat agtgtcacct aaatagcttg     420
gcgtaatcat ggtcatagct gtttcctgtg tgaaattgtt atccgctcac aattccacac     480
aacatacgag ccggaagcat aaagtgtaaa gcctggggtg cctaatgagt gagctaactc     540
acattaattg cgttgcgctc actgcccgct ttccagtcgg gaaacctgtc gtgccagctg     600
cattaatgaa tcggccaacg cgaacccctt gcggccatga gccatattca acgggaaacg     660
tcttgctcga ggccgcgatt aaattccaac atggatgctg atttatatgg gtataaatgg     720
gctcgcgata atgtcgggca atcaggtgcg acaatctatc gattgtatgg gaagcccgat     780
gcgccagagt tgtttctgaa acatggcaaa ggtagcgttg ccaatgatgt tacagatgag     840
atggtcagac taaactggct gacggaattt atgcctcttc cgaccatcaa gcattttatc     900
cgtactcctg atgatgcatg gttactcacc actgcgatcc ccgggaaaac agcattccag     960
gtattagaag aatatcctga ttcaggtgaa aatattgctg atgcgctggc agtgttcctg    1020
cgccggttgc attcgattcc tgtttgtaat tgtcctttta acagcgatcg cgtatttcgt    1080
ctcgctcagg cgcaatcacg aatgaataac ggtttggttg atgcgagtga ttttgatgac    1140
```

-continued

```
gagcgtaatg gctggcctgt tgaacaagtc tggaaagaaa tgcataagct tttgccattc    1200
tcaccggatt cagtcgtcac tcatggtgat ttctcacttg ataaccttat ttttgacgag    1260
gggaaattaa taggttgtat tgatgttgga cgagtcggaa tcgcagaccg ataccaggat    1320
cttgccatcc tatggaactg cctcggtgag ttttctcctt cattacagaa acggcttttt    1380
caaaaatatg gtattgataa tcctgatatg aataaattgc agtttcattt gatgctcgat    1440 gagttttttct aagtgccgat caacgtctca ttttcgccaa agttggccc agggcttccc    1500 ggtatcaaca gggacaccag gatttattta ttctgcgaag tgatcttccg tcacaggtat    1560
ttattcgcga taagctcatg gagcggcgta accgtcgcac aggaaggaca gagaaagcgc    1620
ggatctggga agtgacggac agaacggtca ggacctggat tggggaggcg gttgccgccg    1680
ctgctgctga cggtgtgacg ttctctgttc cggtcacacc acatacgttc cgccattcct    1740
atgcgatgca catgctgtat gccggtatac cgctgaaagt tctgcaaagc ctgatgggac    1800
ataagtccat cagttcaacg gaagtctaca cgaaggtttt tgcgctggat gtggctgccc    1860
ggcaccgggt gcagtttgcg atgccggagt ctgatgcggt tgcgatgctg aaacaattat    1920
cctgagaata aatgccttgg cctttatatg gaaatgtgga actgagtgga tatgctgttt    1980
ttgtctgtta aacagagaag ctggctgtta tccactgaga agcgaacgaa acagtcggga    2040
aaatctccca ttatcgtaga gatccgcatt attaatctca ggagcctgtg tagcgtttat    2100
aggaagtagt gttctgtcat gatgcctgca agcggtaacg aaaacgattt gaatatgcct    2160
tcaggaacaa tagaaatctt cgtgcggtgt tacgttgaag tggagcggat tatgtcagca    2220
atggacagaa caacctaatg aacacagaac catgatgtgg tctgtccttt tacagccagt    2280
agtgctcgcc gcagtcgagc gacagggcga agccctcgag gccgccggcg ttgtggatac    2340
cacgcggaaa acttggccct cactgacaga tgaggggcgg acgttgacac ttgaggggcc    2400
gactcacccg gcgcggcgtt gacagatgag gggcaggctc gatttcggcc ggcgacgtgg    2460
agctggccag cctcgcaaat cggcgaaaac gcctgatttt acgcgagttt cccacagatg    2520
atgtggacaa gctgggggat aagtgccctg cggtattgac acttgagggg gcgcgactact    2580 gacagatgag gggcgcgatc cctgacactt gaggggcaga gtgatgacag atgaggggcg    2640
cacctattga catttgaggg gctgtccaca ggcagaaaat ccagcatttg caagggtttc    2700
cgcccgtttt tcggccaccg ctaacctgtc ttttaacctg cttttaaacc aatatttata    2760
aaccttgttt ttaaccaggg ctgcgccctg gcgcgtgacc gcgcacgccg aagggggtg    2820 ccccccctcc tcgaaccctc ccggggatcg cgaggaagca ccaggaaca gcacttatat    2880 attctgctta cacacgatgc ctgaaaaac ttcccttggg gttatccact tatccacggg    2940 gatatttttta taattatttt ttttatagtt tttagatctt ctttttttaga gcgccttgta    3000 ggcatgtcgt cgtaacctgt agaacggagt aacctcggtg tgcggttgta tgcctgctgt    3060
ggattgctgc tgtgtcctgc ttatccacaa catttttgcgc acggttatgt ggacaaaata    3120
cctggttacc caggccgtgc cggcacgttc cgcaatgctt gcataatgtg gcctgtcaaa    3180
tggacgaagc agggattctg caaaccctat gctactccgt caagccgtca attgtctgat    3240
tcgttaccaa ttatgacaac ttgacggcta catcattcac ttttttcttca caaccggcac    3300 gaaactcgct cgggctggcc ccgtgcattt ttttaaatac tcgcgagaaa tagagttgat    3360
cgtcaaaacc aacattgcga ccgacggtgg cgataggcat ccgggtagtg ctcaaaagca    3420
gcttcgcctg gctgatacgt tggtcctcgc gccagcttaa gacgctaatc cctaactgct    3480
ggcggaaaag atgtgacaga cgcgacggcg acaagcaaac atgctgtgcg acgctggcga    3540
```

```
tatcaagctt atcgaaccgg gctgcatccg atgcaagtgt gtcgctgtcg acgagctcgc    3600
gagctcggac atgaggttgc cccgtattca gtgtcgctga tttgtattgt ctgaagttgt    3660
ttttacgtta agttgatgca gatcaattaa tacgatacct gcgtcataat tgattatttg    3720
acgtggtttg atggcctcca cgcacgttgt gatatgtaga tgataatcat tatcacttta    3780
cgggtccttt ccggtgatcc gacaggttac ggggcggcga cctcgcgggt tttcgctatt    3840
tatgaaaatt ttccggttta aggcgtttcc gttcttcttc gtcataactt aatgttttta    3900
tttaaaatac cctctgaaaa gaaaggaaac gacaggtgct gaaagcgagc tttttggcct    3960
ctgtcgtttc ctttctctgt ttttgtccgt ggaatgaaca atggaagtcc gagctcatcg    4020
ctaataactt cgtatagcat acattatacg aagttatatt cgat                    4064
```

METHOD FOR CONVERTING SINGLE-COPY BAC VECTORS TO CONDITIONAL HIGH-COPY PBAC/ORIHC VECTORS

CROSS-REFERENCE TO RELATED APPLICATIONS

This application claims the benefit of U.S. provisional patent application Ser. No. 60/309,125, filed on Jul. 31, 2001.

STATEMENT REGARDING FEDERALLY SPONSORED RESEARCH OR DEVELOPMENT

Not applicable.

BACKGROUND OF THE INVENTION

Efforts to determine the nucleotide sequence of complete genomes, or a large portion thereof, have traditionally taken a so-called bottom-up approach, including preparing a library of random large DNA clones in yeast artificial chromosomes (YACs), bacterial artificial chromosomes (BACs), P1 or cosmids, followed by random subcloning in M13-like vectors without great reliance upon genome mapping. Among such systems, BACs are at present the preferred vector for maintaining large genomic DNA fragments. BACs are preferred because individual DNA fragments are maintained stably in a single-copy (SC) vector in the host cells, even after 100 or more generations of serial bacterial growth. In contrast, the DNA fragments cloned into YACs tend to be unstable and can yield chimeric clones. It is difficult to recover DNA clones from YACs in a pure form.

BAC (or pBAC) vectors typically accommodate inserts in the range of approximately 30 to 300 kilobase pairs. A widely used BAC vector, pBeloBac11, uses a complementation of the lacZ gene to distinguish insert-containing recombinant molecules from colonies carrying the BAC vector, by color. When a DNA fragment is cloned into the lacZ gene of pBeloBac11, insertional inactivation results in a white colony on X-Gal/IPTG plates after transformation. Kim, U-J et al., "Construction and Characterization of a Human Bacterial Artificial Chromosome Library," Genomics 34:213–218 (1996). Thus, it is now possible to distinguish those colonies that contain BACs with DNA inserts from those that lack inserts. A similar prior vector, pBAC108L, lacked the ability to distinguish insert-containing BACs. Shizuya, H., "Cloning and stable maintenance of 300-kilobase-pair fragments of human DNA in *Escherichia coli* using an F-factor-based vector," P.N.A.S. U.S.A. 89:8794–8797 (1992).

Although these SC vectors are advantageously used to clone large genomic DNA fragments for subsequent analysis, especially sequence analysis, the single copy nature of these vectors is also a limitation in that large numbers of cells containing a BAC clone of interest must be grown to produce a sufficient quantity of DNA for subsequent analysis. It is, of course, possible to amplify portions of a BAC clone of interest using, for example, PCR, but simple amplification of the entire insert from a BAC vector has not previously been possible.

U.S. Pat. No. 5,874,259 discloses conditionally amplifiable BAC vectors into which large genomic DNA fragments can be inserted. The conditionally amplifiable BAC vectors contain, in addition to an origin of replication that maintains the vectors at one copy per cell, a conditional origin of replication (conditional ori) at which replication is initiated in response to a suitable signal in the host cell. After a genomic DNA fragment is inserted into a conditionally amplifiable BAC vector, a large amount of the genomic DNA fragment can be obtained through inducing the replication of the BAC vector from its conditional ori. The vectors in U.S. Pat. No. 5,874,259 can optionally contain a pair of excision-mediating sites (EMS) flanking the conditional ori and a site into which a genomic DNA fragment can be cloned. In this case, the nucleic acid between the EMS can be excised to create a circular plasmid that comprises the genomic fragment insert and can replicate when the conditional ori is induced.

SC BAC vectors, and BAC libraries created using SC BAC vectors (such as pBeloBac11 and pBAC108L), are known. U.S. Pat. No. 5,874,259 discloses methods and vectors for constructing a conditionally amplifiable BAC library. A method for converting existing insert-containing SC BAC clones to conditionally amplifiable BAC clones is needed in the art.

BRIEF SUMMARY OF THE INVENTION

The present invention is summarized in that an SC BAC vector (containing or lacking a DNA insert) is converted in vivo in a host cell into a conditional high-copy (HC) BAC vector by introducing a conditional ori into the SC BAC vector (in vivo retrofitting). The conditional ori is introduced by site-specific recombination between the SC BAC vector and a vector that contains the conditional ori. The host cell used comprises a recombinase (e.g., Cre) that recognizes a site-specific recombination site (e.g., lox) on both the BAC clone and the conditional ori vector. In the presence of the recombinase, the conditional ori-containing vector recombines into the BAC vector and a conditional HC BAC vector is obtained. After the conditional HC BAC vector is produced, the conditional ori donor vector can be optionally eliminated. One may also optionally isolate the conditional HC BAC vector and transfer it to any host cell of interest.

In a preferred embodiment, the recombinase is inducibly and transiently synthesized in the host cell from an expression vector. The recombinase expression vector can also optionally and advantageously eliminate itself from the host cell, as described below.

Thereafter, the conditional HC BAC vector can be amplified to HC number, if desired, by providing the activation signal in the host cell.

The present invention is also summarized in that a host cell carries a polynucleotide vector that comprises a conditional ori and a DNA sequence recognized by a recombinase. The same recombinase-recognition sequence is also present on an SC BAC clone of interest. The host cell also preferably carries a vector that can express the recombinase in the host cell.

BRIEF DESCRIPTION OF THE SEVERAL VIEWS OF THE DRAWINGS

FIG. 2 shows the DNA sequence of a specific retrofitting vector pJW470 that comprises a conditional origin (oriV) and a DNA sequence (loxP) recognized by the site-specific recombinase Cre.

DETAILED DESCRIPTION OF THE INVENTION

Figure 1:
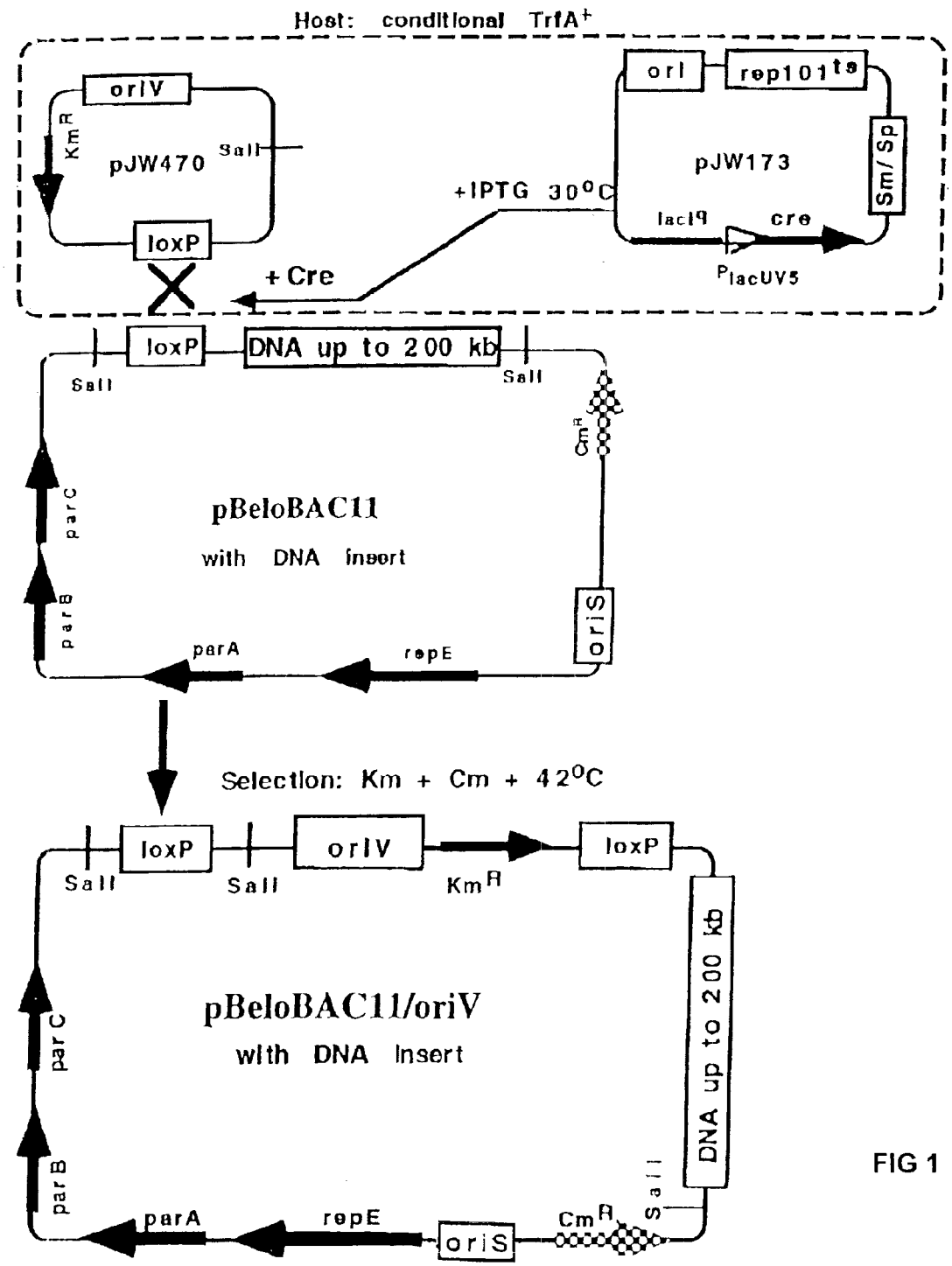
FIG. 1 shows a specific example of converting an SC BAC clone to a conditional HC BAC clone.

An SC BAC vector or a BAC clone in an existing BAC library (referred to herein interchangeably as "BAC vector"

or "BAC clone") can be converted into a conditional HC BAC clone in a suitable host cell by introducing a conditional ori into the SC BAC clone through site-specific recombination between the BAC clone and a vector that contains the conditional ori. The BAC clone and the vector that contains the conditional ori have to be introduced into the host cell first. When either the BAC clone or the conditional ori vector is already in the host cell, the other is introduced into the host cell.

The SC BAC clone that is suitable for conversion by the method of the present invention is one that can replicate independently in the host cell and contains DNA sequences that encode any proteins required for plasmid replication, maintenance, and partitioning that are not otherwise provided in the host cell. The SC BAC clone must also contain a site for site-specific recombination with the conditional ori vector. The conditional ori vector must contain the conditional ori and a site for site-specific recombination with the SC BAC clone. When site-specific recombination is induced in the host cell, a BAC clone that contains the conditional ori, i.e., a conditional HC BAC clone, is obtained. The terms "conditional HC BAC clone" and "conditional amplifiable BAC clone" are used interchangeably herein.

Conditional ori's are known to the art and the details of inducible amplification are not repeated herein. Of course, the conditional ori is chosen for compatibility with a known inducing agent, for its normally tight down regulation in the selected host cells in the absence of the compatible inducing agent, and for its strong inducible operability in the presence of the inducing agent.

The conditional ori, when provided in combination with the compatible inducing agent, has sufficient activity to amplify the vector to a copy number sufficient to produce a desired amount of the DNA insert in the vector. A preferred conditional ori is oriV, although the conditional ori could be any ori that functions in the host cell and is normally inactive until exposed to the replication-inducing agent. OriV has a broad host range, can replicate DNA fragments of 100-kb or larger, can amplify to HC number, and requires only one inducing protein. OriV is induced by the TrfA protein, the structure of which is known to the art. The copy number of the vector can be controlled by the amount of TrfA protein (or a mutant thereof that retains an ability to induce DNA replication, such mutants being known to the art), which in turn can be controlled by the activity level of a promoter. In the presence of TrfA, a vector that comprises oriV is induced to replicate to HC number, such as more than at least about 10 copies per cell, preferably at least about 50 copies per cell, and still more preferably at least about 80 to 100 copies per cell. When the oriV/TrfA system is used, the vector is suited for use in any Gram-negative oriV/TrfA compatible host. Other known conditional origins of replication that can be used in the invention include but are not limited to ori's of various natural plasmids or bacteriophages.

It is preferred but not essential that replication be conditioned upon the presence of a single agent, such as a protein, although multi-agent replication systems are known. If the inducing agent is encoded by polynucleotide, the polynucleotide can be provided in an expression cassette under the transcriptional control of a promoter. The promoter can be an inducible promoter. Such an expression cassette can reside in the genome of the host cell or on a vector in the host cell.

Inducible promoters are known to the art and a detailed summary of the state of the art is not provided herein. A suitable inducible promoter functions in the selected host cell and responds to an inducing agent with sufficient strength to promote the transcription of a downstream heterologous polynucleotide operably linked to the inducible transcriptional promoter. In this patent, "operably linked" means that the promoter is upstream of the polynucleotide coding sequence such that productive transcription of the polynucleotide is initiated at the promoter. "Heterologous" refers to a polynucleotide or polypeptide not natively found in or produced by the host cells. The term "polypeptide" broadly encompasses all proteinaceous molecules including, without limitation, oligopeptides, peptides and proteins, as those terms are understood in the art. Examples of inducible promoters that can be used in the present invention include but are not limited to araC-$P_{araBAD}$ activator/promoter and the tetR-$P_{LtetO}$ repressor/promoter. These two promoters can be activated by treating the host cells with 0.01% L-arabinose (LA) and 100 ng/ml anhydrotetracycline (aTc), Lutz et al., 25 N.A.R. 1203 (1997), respectively. Higher concentrations of LA and aTc can further increase the corresponding promoter's activity. Promoter araC-$P_{araBAD}$ could also be down-regulated by the anti-inducer, d-fucose. Thus, the activity of araC-$P_{araBAD}$ can alternatively be regulated by adjusting the LA/d-fucose ratio. Other suitable inducible promoters known to one of ordinary skill in the art can be used in the present invention.

Both the conditional ori and the inducible promoter can be activated by suitable signals in a host cell. The agents can be positive regulators or can interact with negative regulators to increase amplification and transcription as desired. A positive regulator (inducer) acts by providing a signal that increases an activity while a negative regulator (repressor) prevents an activity until an agent prevents the negative regulation. The agents can be organic or inorganic chemical agents or can be polypeptides encoded by polynucleotide sequences in the host cell genome or on an extrachromosomal vector present in the host cell. Alternatively, the agents can be administered manually to the host cells by, e.g., providing the agent in the growth medium. Preferably, the inducing agent(s) increase transcription and/or replication to an extent proportional to their level in the host cell. The skilled artisan will appreciate that it is within the level of skill in the art to provide as simple or as complex a regulatory scheme as desired for ensuring that the appropriate agent is available to the vector at the appropriate time. The precise nature of that scheme is not critical to the invention. Rather, for purposes of this invention, it is understood that the ultimate agents for amplifying the vector and for inducing transcription can be provided as needed.

A suitable DNA recombinase-recognition sequence on an SC BAC clone that can be used to bring in the conditional ori include those whose recombination is aided by a specific DNA recombinase and the recombination of which will not adversely affect desirable functions of the BAC clone. Examples of such recombination sequences include but are not limited to loxP and FRT. Recombination of loxP sequences is aided by the Cre protein and recombination of FRT sequences is aided by the Flp protein.

The site-specific recombinase can be constitutively expressed or preferably, be transiently induced in the host cell. The recombinase-encoding DNA sequence can reside in the host cell genome or on a vector introduced into the host cell. A vector containing the recombinase gene is hereinafter referred to as the recombinase vector. The inducible expression of a gene has been described above in connection with the inducible expression of an agent that activates a conditional ori.

The method of the present invention involves introducing either a BAC clone, one or more vectors, or both into host cells. Suitable methods for introducing BAC clones and various vectors into a host cell (for example, electroporation or transformation/transfection) are known to one of ordinary skill in the art. To facilitate the process, vectors in the present invention that need to be introduced into a host cell carry selection markers. Any selection marker known to one of ordinary skill in the art can be used in the present invention. Examples of such markers include but are not limited to antibiotic resistance.

After a conditional HC BAC clone is obtained, depending on the subsequent applications, the conditional HC BAC clone may or may not need to be purified. Purifying the conditional HC BAC clone means separating the HC BAC clone vector from the conditional ori vector and if applicable, the recombinase vector. For example, a common subsequent application for the conditional HC clone is to sequence the DNA insert it carries. The sequence primers are usually unique and thus it is not necessary to purify the conditional HC BAC clone. However, if the host cells containing both the conditional HC BAC clone and the conditional ori vector are grown without a signal for activating the conditional ori, it is understood that the conditional ori vector can be eliminated from the host cells.

Preferably, for subsequent use, the conditional HC BAC clone is purified from the conditional ori vector and if applicable, the recombinase vector. One way to achieve this is to eliminate the conditional ori vector and, if applicable, the recombinase vector from the host cells. There are many methods known to one of ordinary skill in the art to eliminate the two vectors from the host cells. Any of these methods can be used. For example, the conditional ori vector can be eliminated simply by growing the host cells without providing the conditional ori activating signal. The conditional HC BAC clone is not lost during such a process because the conditional HC BAC clones also contain a single-copy replication origin (such as oriS) that is compatible with the host cells and requires no induction. The recombinase vector can be eliminated by making replication of the vector temperature sensitive and growing the host cells at a nonpermissive temperature.

When the conditional ori vector and, if applicable, the recombinase vector, are to be eliminated from the host cells, the host cells preferably also contain facility to activate the conditional ori. Host cells that contain suitable facility are known. For example, U.S. Pat. No. 5,847,259, incorporated herein by reference as if set forth in its entirety, describes how to make and how to use the TrfA/oriV system. After the conditional ori vector and the recombinase vector are eliminated, one can grow the host cells and then, when desired, activate the conditional ori on the BAC clone to amplify the BAC clone in each host cell. One can similarly produce large amounts of a protein encoded by the BAC clone by providing on the clone a transcriptional promoter and by activating the promoter, particularly after amplification of the clone.

Another way to separate the conditional HC BAC clone from the conditional ori vector and, if applicable, the recombinase vector, is to purify the conditional HC BAC clones from the host cells and the other two vectors. There are many methods known to one of ordinary skill in the art to achieve this. Any of these methods can be used. For example, a mini-prep can be performed. Alternatively, a unique restriction site can be engineered into the other two vectors, and thus when the vectors and the conditional HC BAC clone are purified from the host cells, the two vectors can be linearized so that they will not transform subsequent host cells along with the conditional HC BAC clones.

Although the method of the present invention has been described so far in the context of converting SC BAC clones in an existing BAC library, it is understood that the same method can be used to convert any SC BAC vector, with or without an insert, to a conditional high-copy version.

A suitable host cell for generating a conditional HC BAC vector and for producing a HC number of the BAC vector can be a bacterium such as an *E. coli* cell and some other suitable cells. One of ordinary skill in the art knows how to create such a suitable cell. Examples of suitable host cells include but are not limited to TransforMax EPI300, also called EPI300 (Epicentre, Madison, Wis.), Stbl-2-trfA (Invitrogen Life Technologies, Carlsbad, Calif.) and GeneHogs-trfA (Invitrogen Life Technologies, Carlsbad, Calif.). Hamilton, C. M., "A Binary-BAC system for plant transformation with high-molecular weight DNA," *Gene* 200:107–116 (1997) describes a BAC vector that can be used in plant cells. In addition, the suitable cell for generating a conditional HC BAC vector and the suitable cell for producing a HC number of the BAC vector used in the present invention can be the same or different.

Some of the materials and methods described above are described in greater detail in U.S. Pat. No. 5,874,259, which is incorporated herein by reference as if set forth in its entirety.

The example below describes a preferred embodiment of the present invention.

EXAMPLE

Materials:

Vector pJW470 carries a recombination DNA sequence LoxP, an inducible high-copy origin of replication oriV, and a kanamycin resistance gene ($Km^R$). The DNA sequence of the pJW470 vector is shown in FIG. 2 and in SEQ ID NO:1. Vector pJW173 carries the cre gene, lacI and $P_{lac}$UV5 to control cre expression, a low copy origin of replication (oriS), gene encoding the temperature-sensitive replication factor (rep $101^{ts}$), and the streptomycin/spectinomycin resistance gene (Sm/Sp). Thus, isopropyl-β-D-thiogalactoside (IPTG) can induce an appropriate host cell containing the pJW173 vector to express the Cre protein.

The pBeloBAC11 clones with DNA inserts used in this example were analogous to those as described in Kim, U-J et al., *Genomics* 34:213–218 (1996). Briefly, the pBeloBAC11 clones carry a loxP sequence, a single-copy origin of replication, a chloramphenicol resistance gene ($Cm^R$), the repE gene, the partition genes para, B and C, and a DNA insert. Four pBeloBAC11 clones were retrofitted: one clone with an *A. thaliana* DNA insert, one clone with a rice DNA insert, and two clones with soil microorganisms DNA inserts. The DNAs were inserted into the pBeloBAC11 vector at the HindIII or NotI site on the vector. The host cell strain is a derivative of *E. coli* DH10B which carries a cassette, consisting of the araC-$P_{araBAD}$ promoter and trfA copy-up mutant gene, inserted at the att site in the chromosome. Synthesis of TrfA, required for oriV replication, occurs only in the presence of an inducer, L-arabinose. Therefore, the host strain is a conditional producer of replication protein TrfA resulting in a conditional replication of plasmids containing oriV.

Methods (Illustrated in FIG. 1):

The host strain was grown in LB at 30° C. The pJW470 vector (FIG. 2) and the pJW173 vector were transformed into the host strain and the resulting host strain was grown at 30° C. in the presence of Km, Sm/Sp, and L-arabinose. The host strain cells containing pJW470 and pJW173 were then transformed with those pBeloBAC11 clones, which were to be retrofitted with oriV. The host strain cells containing pJW470, pJW173, and the pBeloBAC11 clones were grown at 30° C. overnight in the presence of Cm, Km, Sm/Sp, and L-arabinose and then used to inoculate medium containing Cm, Km, but not Sm/Sp and L-arabinose. IPTG was then added to the culture to induce Cre and the incubation was continued at 30° C. for 60 minutes. Next, the culture was transferred to 30° C. to eliminate the Cre-donor plasmid, and grown for 2 hours. Culture was diluted and spread on LB agar plates containing Cm, Km and 0.2% glucose and plates were incubated overnight at 42° C. Individual colonies were the retrofitted pBAC/oriV clones, which were tested for conditional DNA amplification. The presence or the absence of the pJW173 and the pJW470 vectors in the host cells was also determined.

Results:

First, a host cell strain containing pJW173 and pJW470 (FIG. 2) was successfully created. Such a host strain can readily be used to convert an SC BAC clone to a conditional HC BAC clone.

Second, at the end of the experiment, host cells that contain one of the four retrofitted clones under non-induced conditions had a similar level of pBeloBAC11 DNA in comparison to host cells that contain the corresponding unretrofitted clone. Under induced conditions, the former had a much higher level of pBeloBAC11 DNA than the latter. The average copy number of the conditional HC pBeloBAC11 clone in a host cell was around 100 under induced conditions. At the same time, pJW470 and pJW173 vectors were not detected in the host cells. This shows that after site-specific recombination between the pJW470 vector and a pBeloBAC11 clone, culturing cells in the absence of L-arabinose and at a nonpermissive temperature resulted in an elimination of pJW470 and pJW173 from the host cells.

It is understood that the preferred embodiment described above is only illustrative and not intended to confine the invention. Rather, the invention should be construed to be of spirit and scope defined by the appended claims.

We claim:

1. A method for converting a single-copy bacterial artificial chromosome (BAC) vector to a conditional high-copy number BAC vector, the method comprising the steps of:
   providing in a host cell a single-copy BAC vector and a vector that comprises a conditionally active origin of replication (ori-vector) wherein both vectors comprise a site-specific recombinase-recognition sequence recognized by a recombinase; and
   expressing the recombinase in the host cell wherein the recombinase leads to site-specific recombination between the recombinase-recognition sequence on the BAC vector and the ori-vector to generate a conditional high-copy number BAC vector.

2. The method of claim 1, wherein the single-copy BAG vector is selected from the group consisting of pBeloBac11 and pBAC108L.

3. The method of claim 1, wherein the single-copy BAC vector contains a DNA insert.

4. The method of claim 1, wherein the host cell can conditionally activate the conditionally active origin of replication.

5. The method of claim 1, wherein the conditionally active origin of replication is oriV.

6. The method of claim 5, wherein the host cell can express a TrfA protein or a TrfA mutant that retains the ability to induce DNA replication.

7. The method of claim 6, wherein the expression of the TrfA protein or the TrfA mutant is controlled by an inducible promoter.

8. The method of claim 1, wherein the recombinase-recognition sequence and the recombinase are selected from the group consisting of loxP and Cre protein, and FRT and Flp protein.

9. The method of claim 1, wherein the recombinase is transiently expressed.

10. The method of claim 1, wherein the recombinase is expressed from a vector contained in the host cell.

11. The method of claim 1, wherein the conditional high-copy number BAC vector obtained can be induced to replicate to at least 10 copies in a suitable host cell.

12. The method of claim 1, wherein the conditional high-copy number BAC vector obtained can be induced to replicate to at least 50 copies in a suitable host cell.

13. The method of claim 1, wherein the conditional high-copy number BAC vector obtained can be induced to replicate to at least 80 copies in a suitable host cell.

14. The method of claim 1, wherein the conditional high-copy number BAC vector obtained can be induced to replicate to at least 100 copies in a suitable host cell.

15. The method of claim 1 further comprising the step of eliminating the ori-vector from the host cell.

16. The method of claim 1, further comprising the step of purifying the conditional high-copy number BAC vector obtained.

* * * * *